US008739793B2

(12) United States Patent  
Ho

(10) Patent No.: US 8,739,793 B2  
(45) Date of Patent: Jun. 3, 2014

(54) PATIENT INTERFACE DEVICE INCLUDING A COATING ADHESIVE LAYER

(75) Inventor: Peter Chi Fai Ho, Pittsburgh, PA (US)

(73) Assignee: Koninklijke Philips N.V., Eindhoven (NL)

( * ) Notice: Subject to any disclaimer, the term of this patent is extended or adjusted under 35 U.S.C. 154(b) by 867 days.

(21) Appl. No.: 12/743,045

(22) PCT Filed: Nov. 11, 2008

(86) PCT No.: PCT/IB2008/054723

§ 371 (c)(1),
(2), (4) Date: May 14, 2010

(87) PCT Pub. No.: WO2009/066202

PCT Pub. Date: May 28, 2009

(65) Prior Publication Data

US 2010/0229872 A1    Sep. 16, 2010

Related U.S. Application Data

(60) Provisional application No. 60/988,914, filed on Nov. 19, 2007.

(51) Int. Cl.
*A61M 11/00* (2006.01)

(52) U.S. Cl.
USPC ............. 128/206.25; 128/207.18; 128/204.18

(58) Field of Classification Search
USPC ............. 128/201.22–201.24, 204.18, 205.25, 128/205.27–207.18
See application file for complete search history.

(56) References Cited

U.S. PATENT DOCUMENTS

| | | | |
|---|---|---|---|
| 2,254,854 A | 9/1941 | O'Connell | |
| 2,931,356 A | 4/1960 | Schwarz | |
| 3,682,171 A | 8/1972 | Dali | |
| 5,682,881 A | 11/1997 | Winthrop | |
| 6,769,432 B1 | 8/2004 | Keifer | |
| 7,506,649 B2 * | 3/2009 | Doshi et al. | 128/207.18 |
| 2005/0284479 A1 | 12/2005 | Schrader | |
| 2006/0081256 A1 | 4/2006 | Palmer | |

FOREIGN PATENT DOCUMENTS

| | | |
|---|---|---|
| CN | 1363639 A | 8/2002 |
| DE | 10329818 A1 | 1/2005 |
| EP | 1516643 A1 | 3/2005 |
| GB | 2368533 A | 5/2002 |
| WO | WO9925410 A1 | 5/1999 |
| WO | WO0050121 A1 | 8/2000 |
| WO | WO2008019294 A2 | 2/2008 |
| WO | WO2008019294 A3 | 2/2008 |
| WO | WO2008060523 A2 | 5/2008 |
| WO | WO2008060523 A3 | 5/2008 |

* cited by examiner

*Primary Examiner* — Steven Douglas

(74) *Attorney, Agent, or Firm* — Michael W. Haas

(57) ABSTRACT

Various embodiments of a patient interface device, such as a mask (10, 46), nasal pillow (42), or nasal cannula (54, 76, 76', 78, 82, 90 96), that includes an adhesive layer (40) provided on a surface thereof that is structured to temporarily bond to the skin of a user of the patient interface device. The adhesive layer may include a bonding agent, such as a polymer gel, having a residual extraction force of between about 50 grams and about 200 grams.

20 Claims, 13 Drawing Sheets

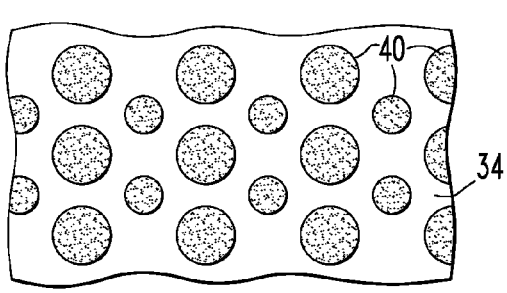
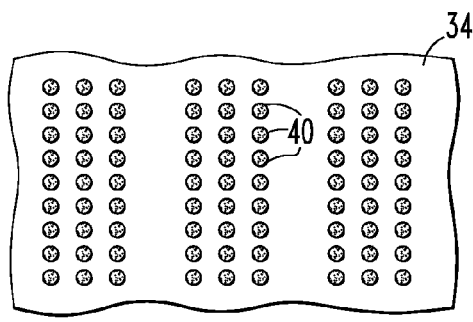
FIG.5A　　　　　FIG.5B
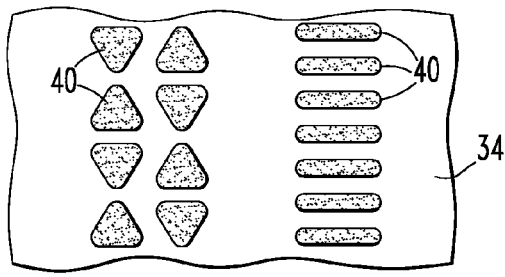
FIG.5C
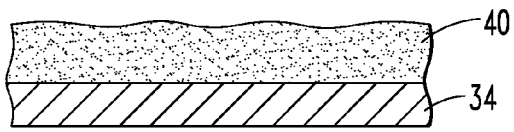
FIG.6A
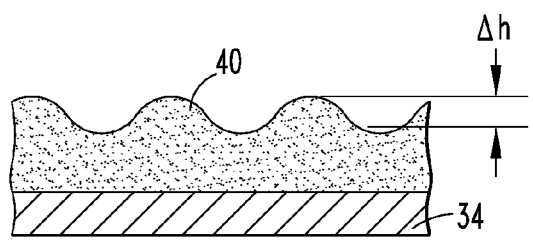
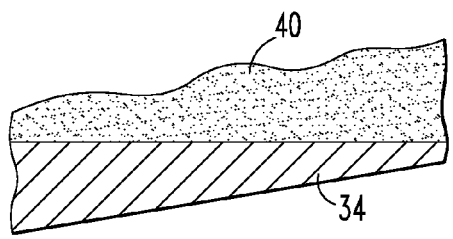
FIG.6B　　　　　FIG.6D
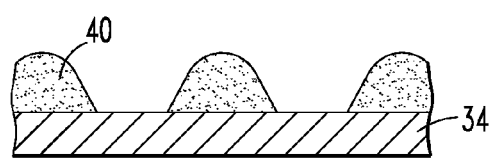
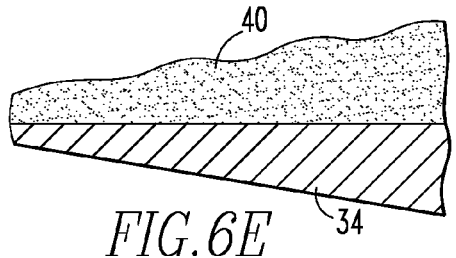
FIG.6C　　　　　FIG.6E

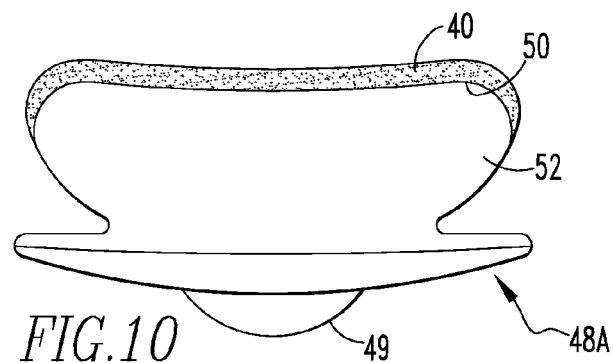
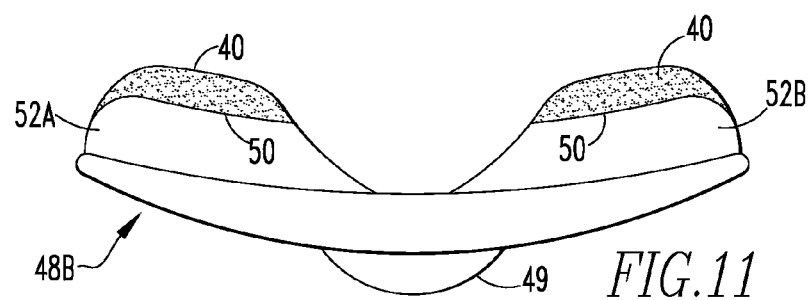
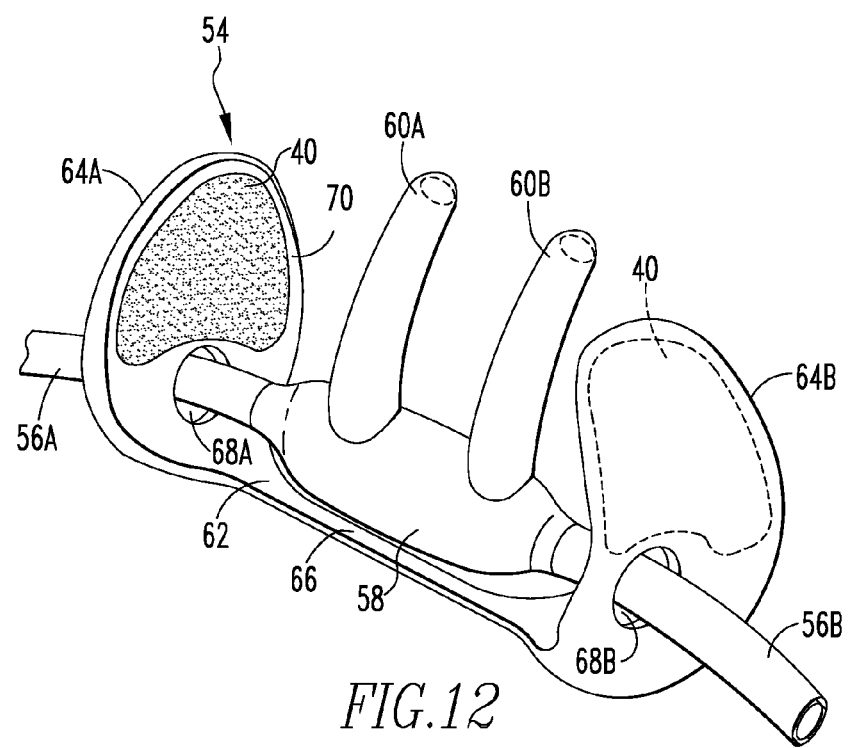

PATIENT INTERFACE DEVICE INCLUDING A COATING ADHESIVE LAYER

The present invention relates to patient interface devices, and in particular to a patient interface device, such as a mask or cannula, that includes one or more coating layers acting as an adhesive and, in certain applications, a sealant.

A variety of respiratory masks are known which have a flexible seal that covers the areas surrounding the nose and/or mouth of a human user and that are designed to create a continuous seal against the user's face. Because of the sealing effect created, gases can be provided at a positive pressure within the mask for consumption by the user. The uses for such masks include high altitude breathing (aviation applications), swimming, mining, fire fighting and various medical diagnostic and therapeutic applications.

One requisite of many of these masks, particularly medical respiratory masks, is that they provide an effective seal against the user's face to prevent leakage of the gas being supplied. Commonly, in conventional mask configurations, a good mask-to-face seal has been attained in many instances only with considerable discomfort for the user. This problem is most crucial in those applications, especially medical applications, which require the user to wear the mask continuously for hours or perhaps even days. In such situations, the user often will not tolerate the mask for long durations and therefore optimum therapeutic or diagnostic objectives will not be achieved, or will be achieved with great difficulty and considerable user discomfort.

Several types of respiratory masks for the types of applications mentioned above are known. Perhaps the most common type of mask incorporates a smooth sealing surface extending around the periphery of the mask and exhibiting a generally uniform, i.e., predetermined or fixed, seal surface contour that is intended to be effective to seal against the user's face when force is applied to the mask with the sealing surface in confronting engagement with the user's face. The sealing surface typically consists of an air or fluid filled cushion, or it may simply be a molded or formed surface of a resilient seal element made of an elastomer such as plastic, rubber, silicone, vinyl or foam.

Such masks have performed well when the fit is good between the contours of the seal surface and the corresponding contours of the user's face. This may occur, for example, if the contours of the user's face happen to match well with the predetermined contours of the seal. However, if the seal fit is not good, there will be gaps in the seal-to-face interface resulting in gas leaking from the mask at the gaps. Considerable force will be required to compress the seal member to close the gaps and attain a satisfactory seal in those areas where the gaps occur. Such force is undesirable because it produces high pressure points elsewhere on the face of the user where the mask seal contour is forcibly deformed against the face to conform to the user's facial contours. This will produce considerable user discomfort and possible skin irritation and breakdown anywhere the applied force exceeds the local perfusion pressure, which is the pressure that is sufficient to cut off surface blood flow. Ideally, contact forces should be limited between the mask and the user's face to avoid exceeding the local perfusion pressure, even at points where the mask seal must deform considerably.

The problem of seal contact force exceeding desirable limits is even more pronounced when the positive pressure of the gas being supplied is relatively high or is cyclical to relatively high levels. Because the mask seals by virtue of confronting contact between the mask seal and the user's face, the mask must be held against the face with a force sufficient to seal against leakage of the peak pressure of the supplied gas. Thus, for conventional masks, when the supply pressure is high, head straps or other mask restraints must be relatively tightly fastened. This produces high localized pressure on the face, not only in the zone of the mask seal, but at various locations along the extent of the retention straps as well. This, too, will result in discomfort for the user after only a brief time. Even in the absence of excessive localized pressure points, the tight mask and head straps may become uncomfortable, and user discomfort may well cause discontinued cooperation with the treatment regimen. Examples of respiratory masks possessing continuous cushion sealing characteristics of the type just described are provided in U.S. Pat. Nos. 2,254,854 and 2,931,356.

In addition, nasal cannulas are used in a variety of clinical situations such as oxygen delivery, gas sampling (e.g., carbon dioxide), and pressure measurement. Nasal cannulas and similar devices are generally retained in place by the tension resulting from looping the associated tubing or cable over the patient's ears, which often creates discomfort. Patient movement resulting from the discomfort may cause the nasal cannula to become dislodged.

There is thus room for improvement in the area of mask, cannulas, and similar patient interface devices.

In one embodiment, the invention provides a patient interface device, such as a mask or nasal pillow, that includes at least one seal element and an adhesive layer provided on an outer surface of the at least one seal element. The adhesive layer is structured to temporarily bond to the skin of the user of the patient interface device and comprises a bonding agent having a residual extraction force of between about 50 grams and about 160 grams. The bonding agent may be a cross linked polymer gel, such as a silicone gel or a polyurethane gel. In one particular embodiment, the adhesive layer further includes a coating layer formed by co-curing the bonding agent with at least one layer of a primer material. The adhesive layer may comprise at least one generally annular strip, of uniform or varying width, and in particular may be a plurality of concentric generally annular strips. Furthermore, the adhesive layer may have a generally uniform height, or, alternatively, may have a varying height. In one particular embodiment, the adhesive layer comprises a plurality of deposits of the bonding agent provided on the outer surface of the at least one seal element. Such deposits may have similar or differing sizes, and may have similar or differing geometric shapes (such as circular, triangular or oblong shapes).

Another embodiment provides a patient interface device that includes a mask having a body, at least one seal element coupled to the body, a facial support having an engagement surface coupled to the body, and an adhesive layer provided on the engagement surface, the adhesive layer comprising a bonding agent having a residual extraction force of between about 50 grams and about 160 grams. This patient interface device may or may not also include an adhesive layer on a sealing element of the mask.

In another embodiment, a nasal cannula is provided that includes one or more nasal inserts for delivering a fluid to the nasal passageway of a user, at least one attachment panel, and an adhesive layer provided on the at least one attachment panel and being structured to temporarily bond to the skin of the user, the adhesive layer comprising a polymer gel such as a silicone gel or a polyurethane gel. The adhesive layer may further include a coating layer formed by co-curing the polymer gel with at least one layer of a primer material. In the preferred embodiment, the polymer gel has a residual extraction force of between about 50 grams and about 160 grams. In another particular embodiment, the nasal cannula includes a fluid delivery tube in fluid communication with the one or more nasal inserts. In this embodiment, the fluid delivery tube is inserted through one or more apertures provided in the at least one attachment panel, whereby the at least one attachment panel is free to move relative to the fluid delivery tube prior to being temporarily bonded to the skin of the user. In still another particular embodiment, the nasal cannula includes a first fluid delivery tube and a second fluid delivery tube in fluid communication with the one or more nasal inserts, wherein the at least one attachment panel comprises a first attachment panel and a second attachment panel connected to one another by a connecting strip, In this embodiment, the first fluid delivery tube is inserted through an aperture provided in the first attachment panel and the second fluid delivery tube is inserted through an aperture provided in the second attachment panel, whereby the first attachment panel is free to move relative to the first fluid delivery tube and the second attachment panel is free to move relative to the second fluid delivery tube.

In yet another embodiment, the invention provides a nasal cannula that includes one or more nasal inserts for delivering a fluid to the nasal passageway of a user, a fluid delivery barrel in fluid communication with the one or more nasal inserts, and an adhesive layer provided on one or more outer surfaces of the fluid delivery barrel and being structured to temporarily bond to the skin of the user, the adhesive layer comprising a polymer gel such as a silicone gel or a polyurethane gel. The adhesive layer may further include a coating layer formed by co-curing the polymer gel with at least one layer of a primer material. In the preferred embodiment, the polymer gel has a residual extraction force of between about 50 grams and about 160 grams.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

The accompanying drawings illustrate presently preferred embodiments of the invention, and together with the general description given above and the detailed description given below, serve to explain the principles of the invention. As shown throughout the drawings, like reference numerals designate like or corresponding parts.

FIGS. 5A, 5B and 5C are schematic diagrams showing the adhesive layer of the present invention in the form of a pattern of deposits of a bonding agent on a sealing element;

FIGS. 6A through 6E are schematic diagrams of various embodiments of an adhesive layer of the present invention;

FIGS. 10 and 11 are top plan views of forehead supports forming a part of a mask according to alternative embodiments;

FIG. 12 is an isometric view of a patient interface device in the form of a nasal cannula according to further embodiment of the invention;

Figure 1:
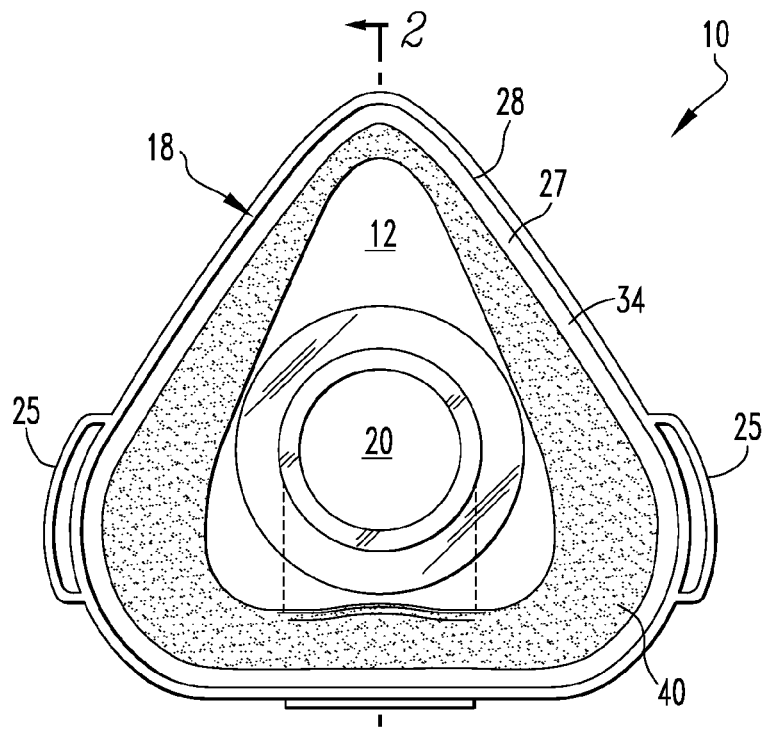
FIG. 1 is a front elevational view.

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

As employed herein, the term "patient interface device" refers to any suitable mechanism for transporting gas to and/or from the airway of a patient and expressly includes, but is not limited to, non-invasive patient interfaces such as masks (e.g., without limitation, masks including support elements such as forehead supports and cheek pads and full face masks such as the Total™ face mask sold by the assignee hereof), nasal cannulas, nasal masks (including tip of the nose masks such as the Simplicity™ and Comfort Lite masks sold by the assignee hereof), combination nasal/oral masks and nasal pillows.

As employed herein, the statement that two or more parts or components are "coupled" together shall mean that the parts are joined or operate together either directly or through one or more intermediate parts or components.

As employed herein, the term "number" shall mean one or more than one and the singular form of "a", "an", and "the" include plural referents unless the context clearly indicates otherwise.

Figure 2:
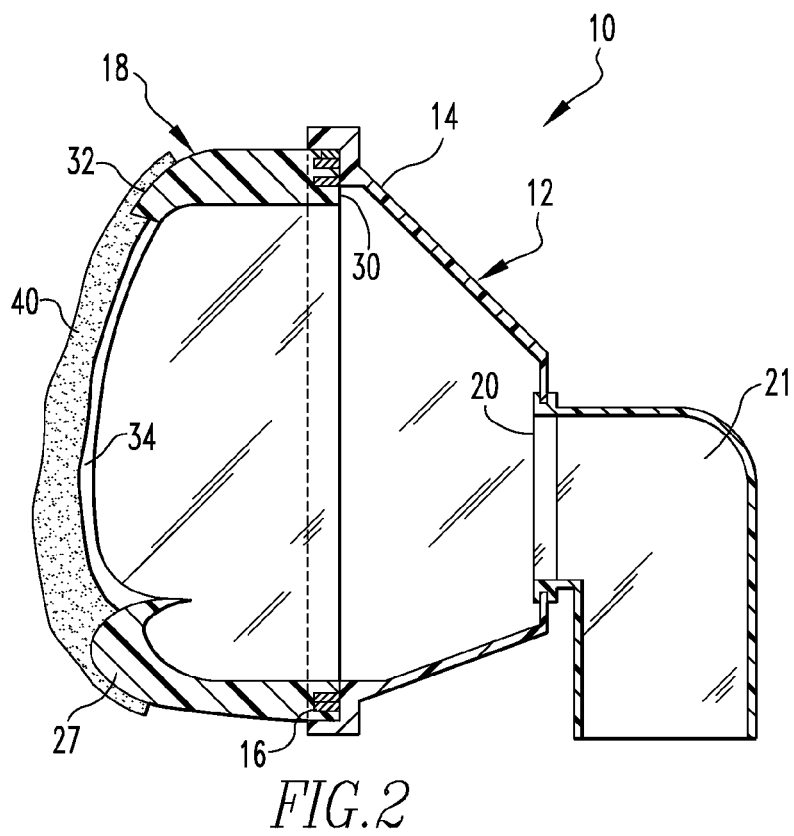
FIG. 2 is a cross sectional view of a respiratory mask according to an embodiment of the invention.

FIG. 1 is a front elevational view and FIG. 2 is a cross sectional view of a respiratory mask 10 according to an embodiment of the invention. The respiratory mask 10 includes a shell or body 12 having an open side 14 that defines a generally annular surface 16 to which is sealingly affixed a seal element 18. The mask body 12 is preferably, although not necessarily, a generally rigid shell, whereas the seal element 18 is a flexible, resilient unitary member made of, for example, an elastomer such as plastic, rubber, silicone, vinyl or foam.

The mask body 12 also defines an opening 20 to which there is attached a fluid coupling device, such as a swivel conduit 21 (FIG. 2), for carrying fluid, such as a breathing gas, between the chamber within the mask 10 and an external gas source (not shown), such as a blower or other suitable device. It is to be understood that the present invention contemplates a variety of different fluid coupling devices that could be attached, either permanently or selectively, to the opening 20 to carry fluid to or from the chamber defined by the mask 10.

The mask 10 shown in FIGS. 1 and 2 is a nasal mask that accommodates the nasal regions of the user's face. It is to be understood, however, that the present invention also contemplates other patient interface devices such as, without limitation, a full face or an oral/nasal mask that accommodates both the mouth and nose of a user or a total face mask that accommodates substantially the entire facial area of the patient. As is conventional, the mask body 12 also preferably includes fastening devices, such as tabs 25 or the like, that connect to suitable adjustable retention straps (not shown) for retaining the mask with respect to the user's face. Although two such devices are illustrated in FIGS. 1 and 2 and are generally arrayed at selected corners of the mask 10, it is to be understood that other configurations, arrangements, numbers (including none) and locations of fastening devices can be provided without deviating from the principles of the present invention. Although not illustrated, the present invention contemplates providing one or more exhaust ports or other venting mechanisms at a location or locations, such as in the seal element 18, the mask body 12, the conduit 21 or at a junction between these components, to exhaust gas expired by the user to atmosphere.

The seal element 18 includes a solid, yet highly resilient and self-sustaining compressible, generally annular member 27 comprising a peripheral wall portion 28 having a generally annular base or inner end 30 configured so as to substantially match the surface 16 of the mask body 12 to which it is attached. The peripheral wall portion 28 further establishes an outer end 32 generally opposite inner end 30. The outer end 32 defines a generally annular contoured surface 34. The contour of surface 34 is preformed to closely approximate the surface contour of a user's facial structure, especially in the areas of the bridge of the nose, the cheeks adjacent the nose, the space intermediate the nose and upper lip, and the intervening areas contiguous to these. It is to be understood that the contour of the surface 34 can have alternative configurations depending on the type of mask to which the seal element 18 is attached. For a full face mask, for example (not illustrated), the surface 34 may be contoured to accommodate the user's chin in lieu of the area intermediate the nose and upper lip. In either case, variation in the user's facial structure, especially in the area of the bridge of the nose, for example, makes considerable flexibility of the seal element 18 desirable to accommodate the many different facial contours likely to be encountered.

According to an aspect of the present invention, an adhesive layer 40 made of a bonding agent is provided on and bonded to the contoured surface 34 of the annular member 27 of the seal element 18. The adhesive layer 40 has a level of stickiness that will cause it to temporarily bond to the skin of the user of the mask 10, preferably without leaving a significant amount of residue when removed. The adhesive layer 40 will thus provide a bonding seal between the mask 10 and the user's skin so as to reduce and/or eliminate leaks. In addition, with the sealing bond provided by the adhesive layer 40, the strapping forces (through the tabs 25 or the like) can be reduced. For example, a mask may need a smaller number of straps than would be needed without the adhesive layer 40. In fact, in some applications (e.g., flow pressures of 8 cm $H_2O$ or less), the adhesive layer 40 may eliminate the need for strapping altogether.

In the preferred embodiment, the bonding agent of the adhesive layer 40 will have a residual extraction force of between about 50 grams and about 200 grams, and most preferably between about 50 grams and about 160 grams. As used herein, the term residual extraction force means the force required to pull a probe about 12.7 mm (about 0.5 inches) round from the subject material when the probe has been inserted to a depth of about 10 mm (about 0.3937 inches) in a container about 60 mm (about 2.362 inches) in diameter and about 45 mm (about 1.772 inches) deep that is filled with the subject material. In one particular embodiment, the bonding agent of the adhesive layer 40 is a cross linked polymer gel (most preferably with no plasticizer) such as, without limitation, a silicone gel or a polyurethane gel. As is known, a general purpose silicone gel typically has a residual extraction force of 8 to 15 grams. In one preferred embodiment, the bonding agent of the adhesive layer 40 is a silicone gel having a residual extraction force of about 160 grams, which is ten fold stickier than the general purpose silicone gel.

Due to the soft nature of the adhesive layer 40, it is possible that in some applications, a small amount of the adhesive layer 40 may separate therefrom under physical rubbing and be left on the user's skin as a residual material. In order to avoid this phenomenon, the adhesive layer 40 in one particular embodiment may further include a coating layer formed by co-curing the bonding agent with layer of a primer material that will resist material separation. For example, and without limitation, in the case where the bonding agent of the adhesive layer 40 is a silicone gel, any non-gel based silicone, such as a soft RTV-2 material or an LSR (liquid silicone rubber) material can be used as the primer, and the case where the bonding agent of the adhesive layer 40 is a polyurethane gel, a solvent such as acetone can be used as the primer.

Figure 3:
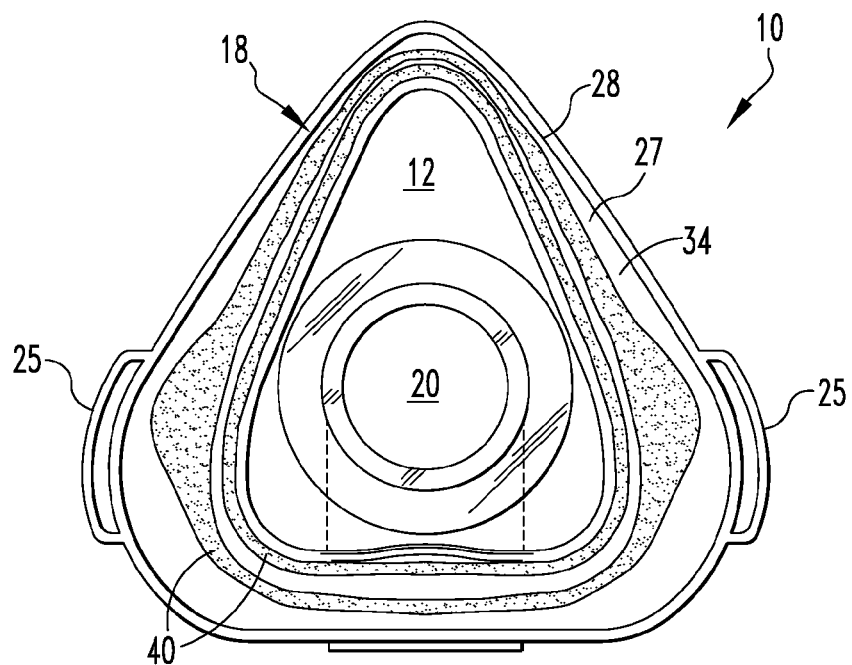
FIGS. 3 and 4 are front elevational views of a respiratory mask according to alternate embodiments of the invention.
Figure 4:
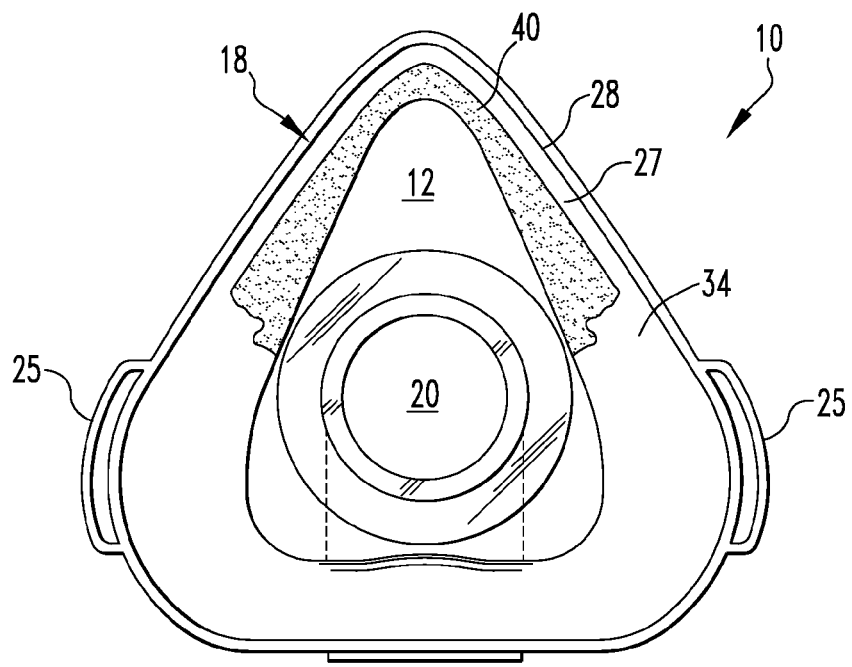

In the embodiment shown in FIGS. 1 and 2, the adhesive layer 40 is a single, generally annular strip having a generally uniform width provided on the contoured surface 34 of the annular member 27 of the seal element 18. It is to be understood that this is meant to be exemplary only, and that many other configurations are possible for the adhesive layer 40. For example, as shown in FIG. 3, the adhesive layer 40 may comprise two or more generally annular portions or strips (of generally uniform or varying widths), or as shown in FIG. 4, the adhesive layer 40 may comprise a non-annular layer (of a generally uniform or varying width), covering only a portion of the contoured surface 34 of the annular member 27 of the seal element 18. In one particular embodiment, a generally annular relatively thin strip forming the adhesive layer 40 may be provided at the outer edge of the contoured surface 34 in order to provide effective sealing enhancement without making the entire contoured surface 34 sticky. Many other configurations are also possible. For example, and without limitation, as seen in FIGS. 5A, 5B and 5C, the adhesive layer 40 may be in the form of a series or matrix or pattern (uniform or varying) of differently sized (FIG. 5A) or similarly sized (FIGS. 5B and 5C) generally circular, oblong and/or triangular deposits of the bonding agent. Other geometric shapes are also possible.

Furthermore, the height of the adhesive layer 40 (or portions thereof) can have various attributes for achieving different results. For example, as shown in FIG. 6A, the height of the adhesive layer 40 can be generally uniform, resulting in a generally smooth surface that maximizes adhesion. A typical height may be on the order of about 0.010 inches (about 0.254 millimeters) to about 0.125 inches (about 3.175 millimeters), although other heights are possible and will depend on the particular application. Alternatively, as shown in FIG. 6B, the height of the adhesive layer 40 can be varied over the area of the adhesive layer 40, resulting in a surface that provides enhanced surface venting and makes the adhesive layer 40 easier to peel from the skin of the user. These latter attributes will also be provided by the configuration of the adhesive layer 40 shown in FIG. 6C, which comprises a pattern of generally circular deposits (i.e., mounds) of the bonding agent. In addition, the contoured surface 34 is often designed to have uneven wall thickness to promote softness and different flexibilities. Therefore, depending on the desired results, the height of the adhesive layer 40 can vary with the thickness of the contoured surface 34. For example, as shown in FIG. 6D, the height of the adhesive layer 40 may increase while the thickness of the contoured surface 34 decreases. This will enhance the bonding even at thinner sections of the contoured surface 34 without changing the overall feel (softness) of the mask 10. Furthermore, as shown in FIG. 6E, the height of the adhesive layer 40 may increase while the thickness of the contoured surface 34 also increases. This will maintain a more flexible structure.

Figure 7:
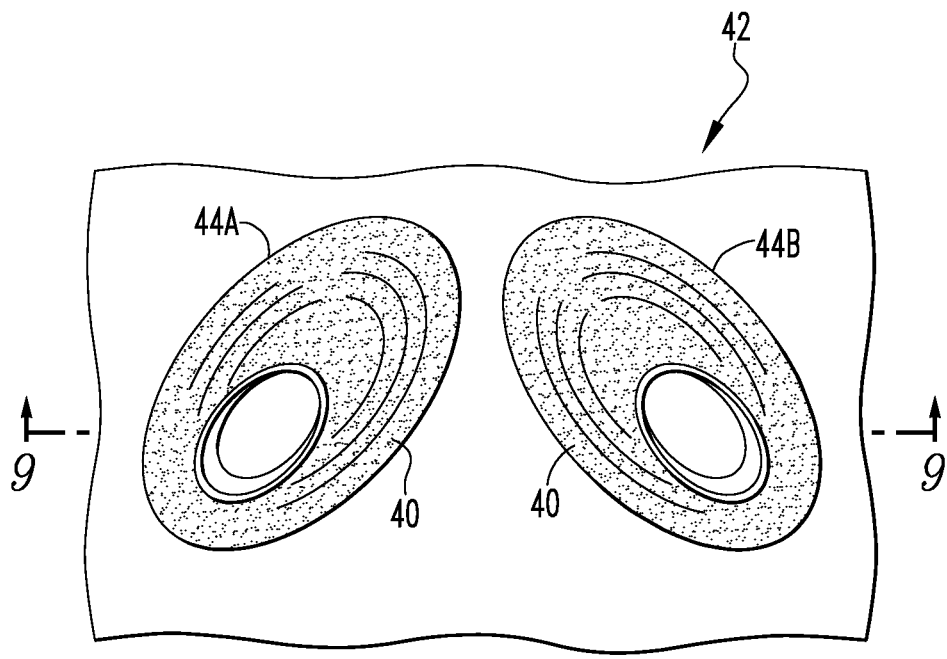
FIGS. 7 and 8 are top plan and cross sectional views, respectively, of a patient interface device in the form of a nasal pillow according to another embodiment of the invention.
Figure 8:
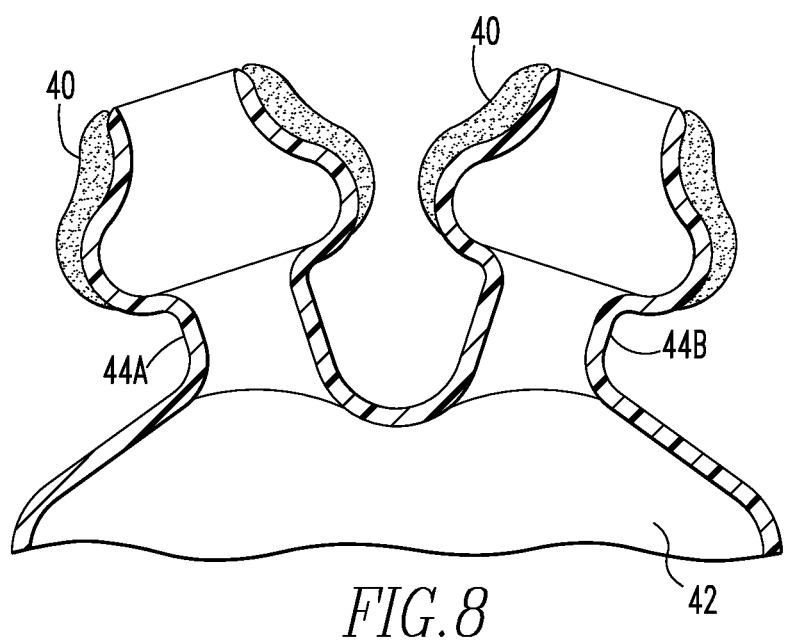

FIGS. 7 and 8 are top plan and cross sectional views, respectively, of a patient interface device in the form of a nasal pillow 42 according to another embodiment of the invention. The nasal pillow 42 includes first and second naris members 44A and 44B having top surfaces in the form of seal elements structured to engage the exterior surfaces of the nares of the nose of a user to deliver a fluid, such as air or oxygen, to the nasal passageway of the user. As seen in FIGS. 7 and 8, the top surface of each naris member 44A, 44B is provided with an adhesive layer 40 as described elsewhere herein. The adhesive layer 40 of each naris member 44A, 44B will thus provide a bonding seal between the nasal pillow 42 and the user's skin at the exterior surfaces of the nares.

Figure 9:
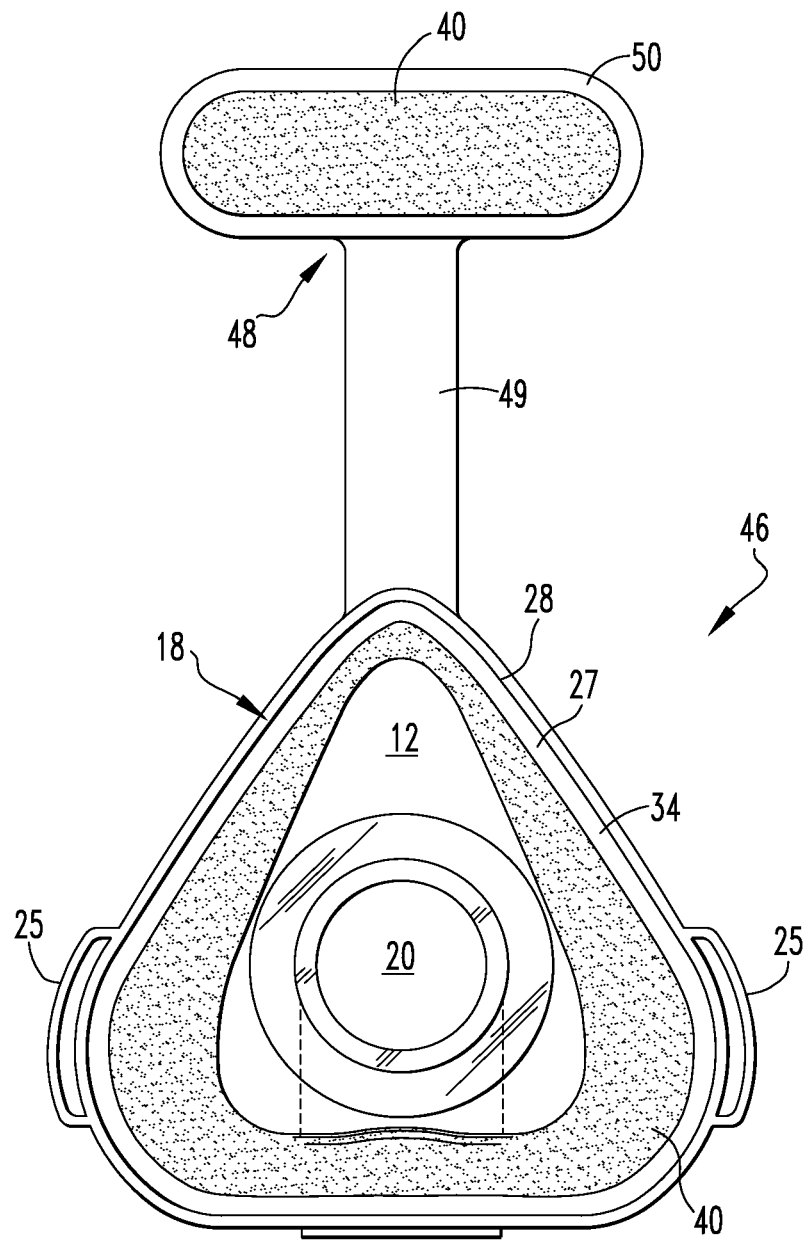
FIG. 9 is a front elevational view of a mask according to yet another embodiment of the invention.

FIG. 9 is a front elevational view of a mask 46 according to yet another embodiment of the invention. The mask 46 is similar to the mask 10, and therefore, as seen in FIG. 9, includes a number of the same parts. The mask 46 further includes a forehead support 48 connected to and extending from the mask body 12 through a support arm 49. The forehead support 48 includes an engagement surface 50 structured to engage the forehead of the user. In prior masks, such an engagement surface 50 would have two top straps extending therefrom in order to help to hold the mask in place. In the embodiment of the mask 46 shown in FIG. 9, no such straps are provided. Instead, an adhesive layer 40 is provided on the engagement surface 50 in order to provide a bonding seal between the forehead support 48 and the user's skin. FIGS. 10 and 11 are top plan views of forehead supports 48A and 48B according to alternative embodiments. The forehead support 48A includes a hollow silicone rubber structure 52 having an engagement surface 50 on which an adhesive layer 40 is provided. The forehead support 48B includes a pair of hollow silicone rubber structures 52A and 52B each having an engagement surface 50 on which an adhesive layer 40 is provided. Although forehead supports 48, 48A and 48B are shown for illustrative purposes as one particular type of facial support, it should be understood that other types of facial supports, such as, without limitation, cheek pads, are also possible.

FIG. 12 is an isometric view of a patient interface device in the form of a nasal cannula 54 according to further embodiment of the invention. The nasal cannula 54 includes fluid delivery tubes 56A and 56B connected to opposite ends of a fluid delivery barrel 58. The fluid delivery tubes 56A and 56B are in fluid communication with a source of fluid (not shown), such as an oxygen source, and deliver the fluid, e.g., oxygen, from the source to the fluid delivery barrel 58. First and second nasal inserts 60A and 60B are in fluid communication with the fluid delivery barrel 58. The first and second nasal inserts 60A and 60B are structured to be received in the nares of a user so that the fluid, e.g., oxygen, can be delivered from the fluid delivery barrel 58 to the nasal passageway of the user. The nasal cannula 54 further includes an attachment mechanism 62 for removeably attaching the nasal cannula 54 to the user's face to assist in holding the nasal cannula 54 in place while in use. In particular, the attachment mechanism 62 includes a first attachment panel 64A and a second attachment panel 64B connected to one another by a connecting strip 66. As seen in FIG. 12, each attachment panel 64A, 64B includes an aperture 68A, 68B which receives therethrough a respective one of the fluid delivery tubes 56A and 56B in order to moveably couple the attachment mechanism 62 to the remainder of the nasal cannula 54. Each attachment panel 64A, 64B includes an inner surface 70 which has provided thereon an adhesive layer 40 in any of the forms described elsewhere herein.

Figure 13:
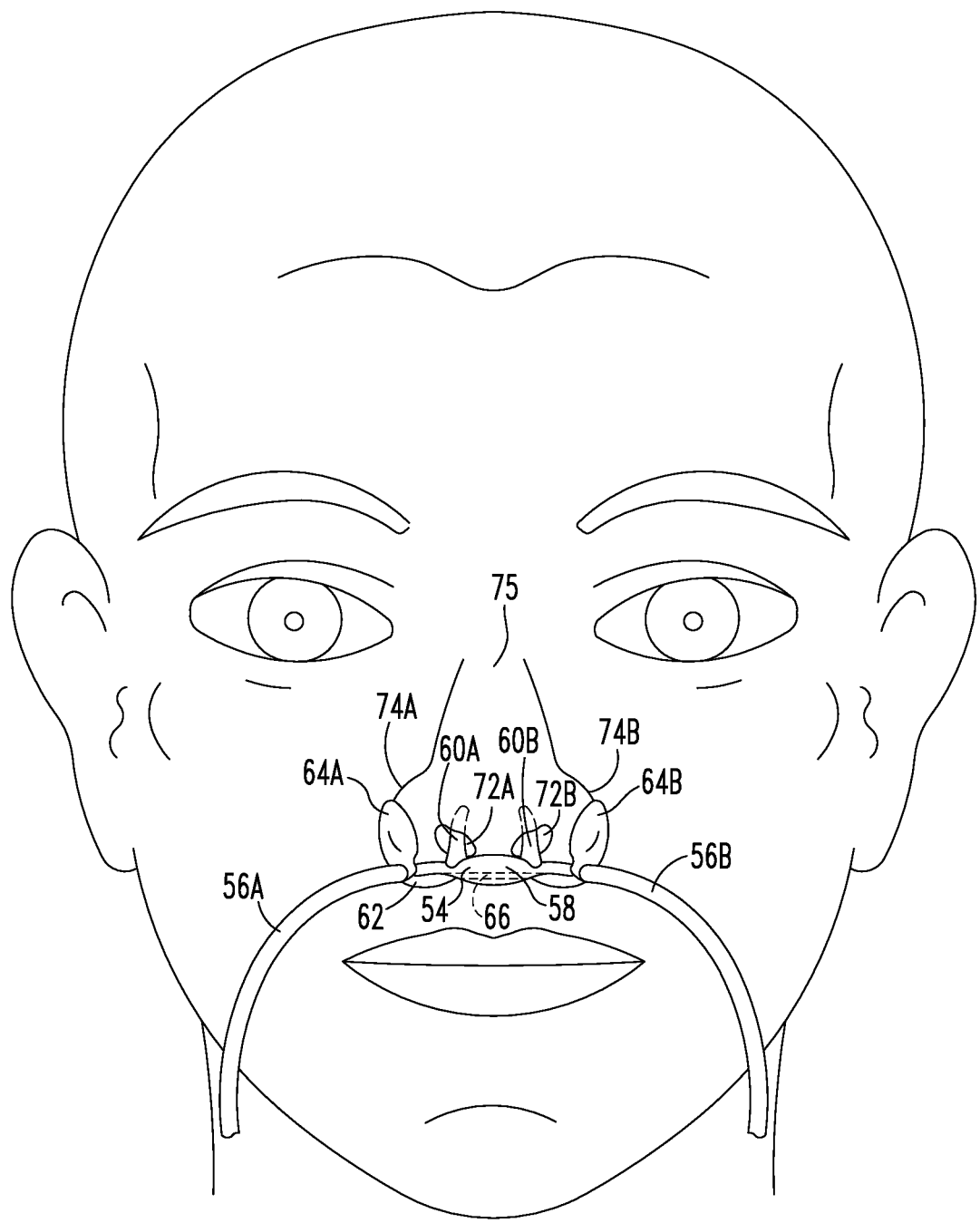
FIG. 13 is a schematic diagram showing the patient interface device of FIG. 12 in use.

Referring to FIG. 13, when in use, the first and second nasal inserts 60A and 60B are inserted within the nares 72A and 72B of the user. In that position, the attachment panels 64A and 64B are able to be removeably adhered to the alar sidewalls 74A and 74B of the nose 75 of the user. Specifically, the adhesive layers 40 provided on the inner surfaces 70 of the attachment panels 64A and 64B are able to be removeably adhered to the alar sidewalls 74A and 74B. As a result, the nasal cannula 54 is securely held in place while in use. As will be appreciated, each of the components of the nasal cannula 54 may be molded out of a polymeric material such as, without limitation, silicone rubber or urethane.

Figure 14A:
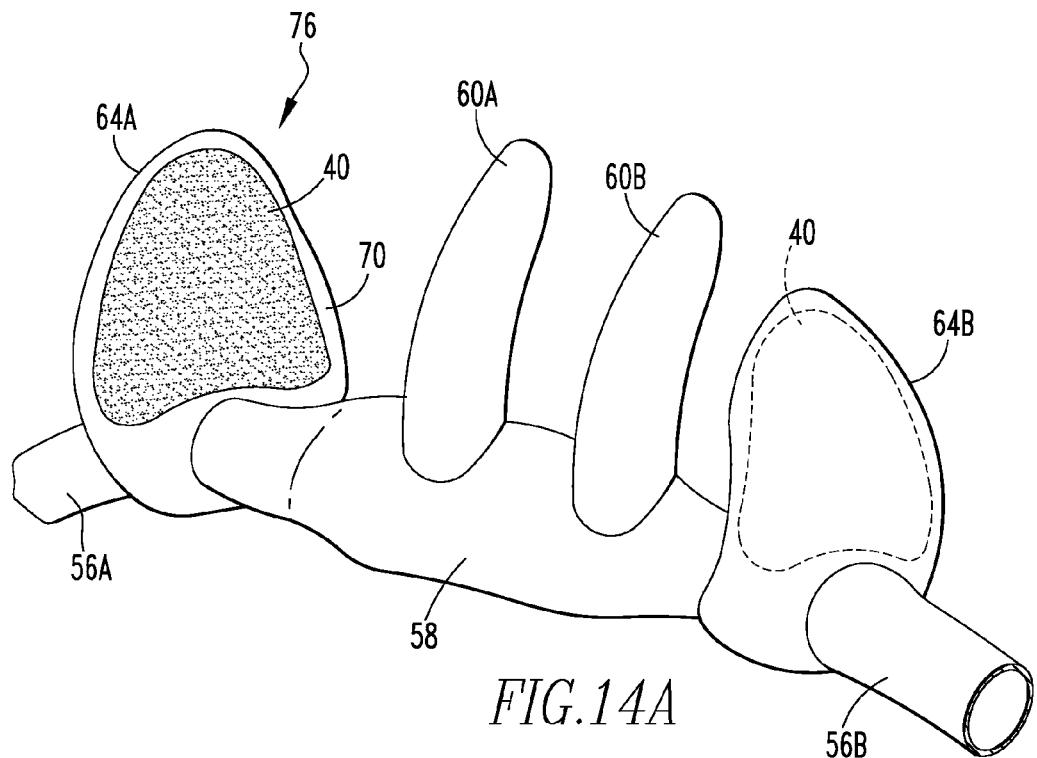
FIG. 14A is an isometric view of a patient interface device in the form of a nasal cannula according to an alternate further embodiment of the invention.
Figure 14B:
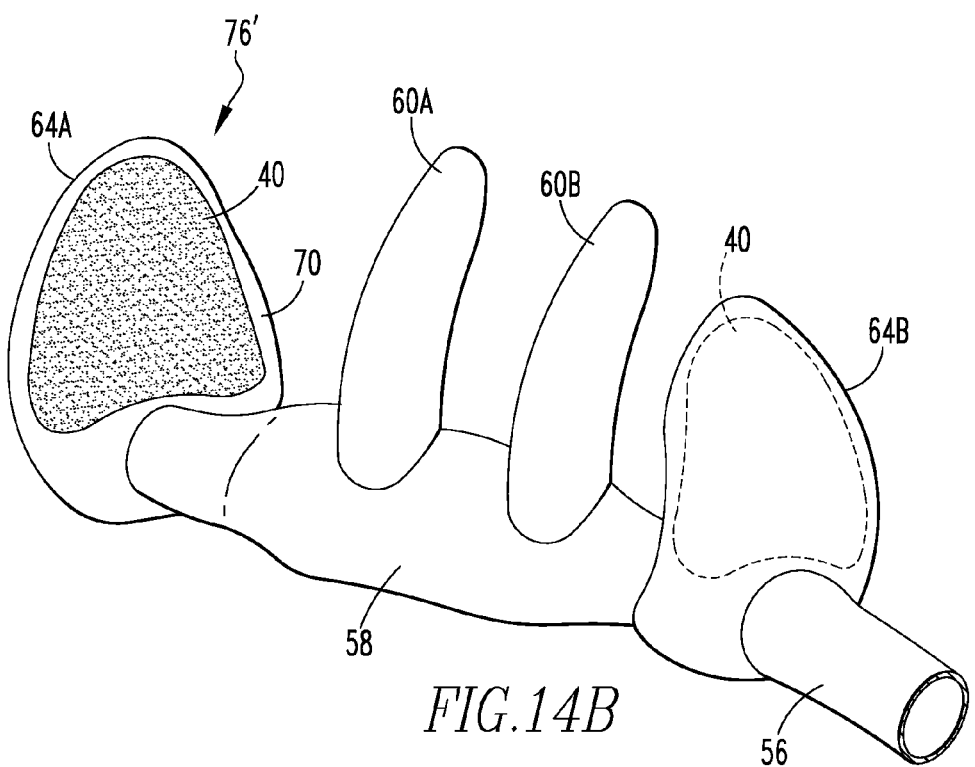
FIG. 14B is an isometric view of a nasal cannula according to an alternative embodiment which is a variation of the nasal cannula shown in FIG. 14A wherein only a single fluid delivery tube is employed.
Figure 15:
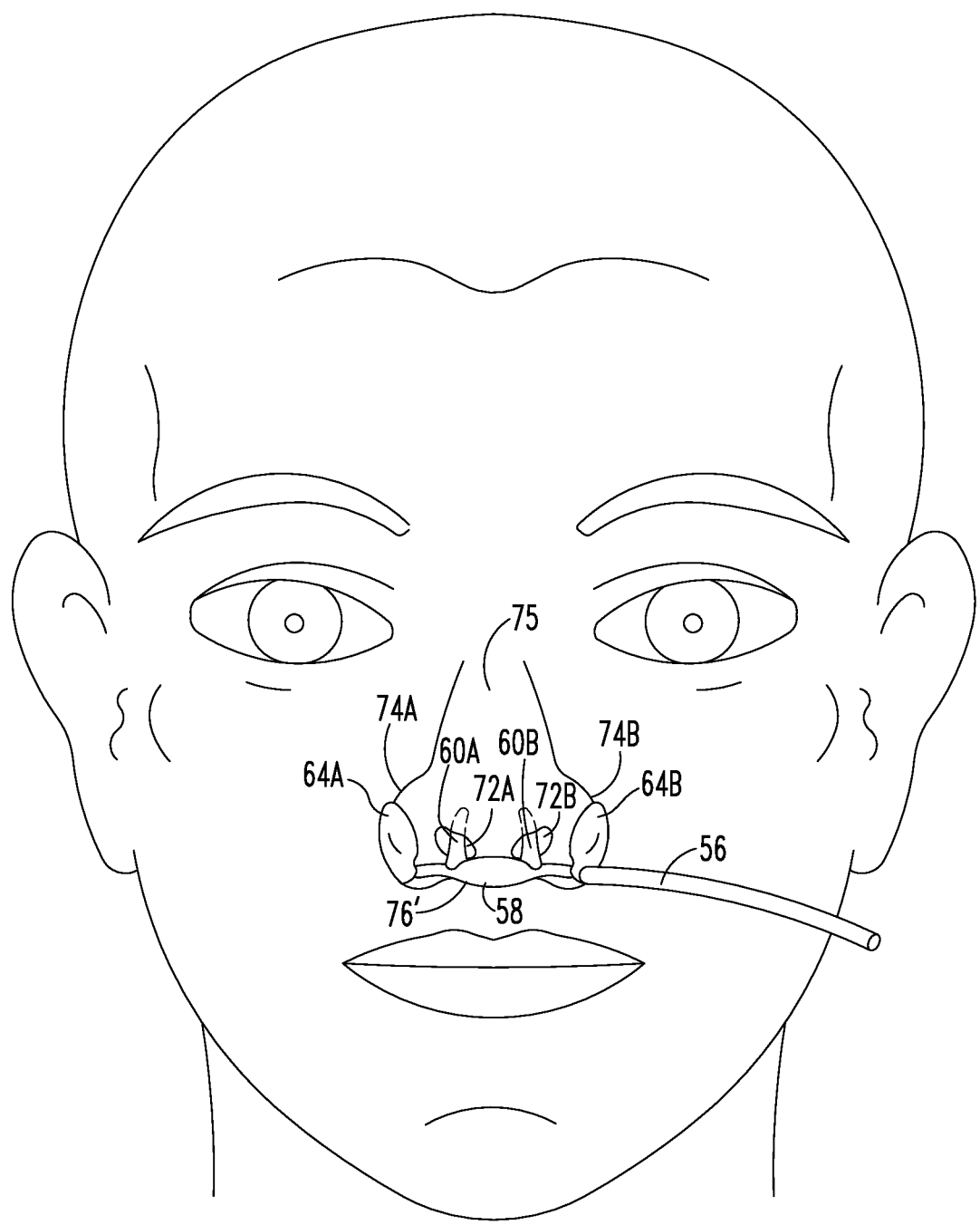
FIG. 15 is a schematic diagram showing the nasal cannula of FIG. 14B in use.

FIG. 14A is an isometric view of a patient interface device in the form of a nasal cannula 76 according to an alternate further embodiment of the invention. The nasal cannula 76 is similar to the nasal cannula 54 and, as seen in FIG. 14A, therefore includes a number of the same components. In nasal cannula 76, however, the attachment panels 64A and 64B are directly affixed on opposite sides of the fluid delivery barrel 58 to respective fluid delivery tubes 56A and 56B. FIG. 14B is an isometric view of a nasal cannula 76' according to an alternative embodiment which is a variation of the nasal cannula 76 shown in FIG. 14A wherein only a single fluid delivery tube 56 is employed. FIG. 15 is a schematic diagram showing the nasal cannula 76' in use wherein the adhesive layers 40 provided on the inner surfaces 70 of the attachment panels 64A and 64B are removeably adhered to the alar sidewalls 74A and 74B of the nose 75 of the user.

Figure 16A:
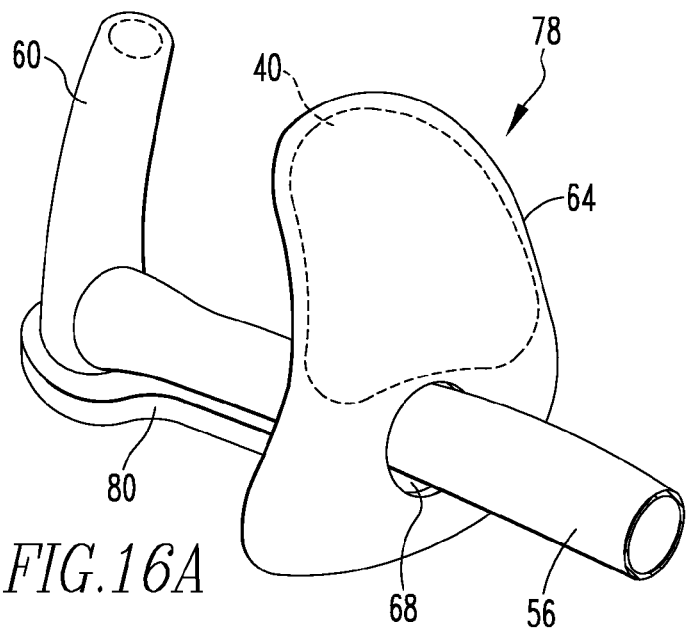
FIGS. 16A and 16B are isometric views of a nasal cannula according to a further alternate embodiment of the present invention.
Figure 16B:
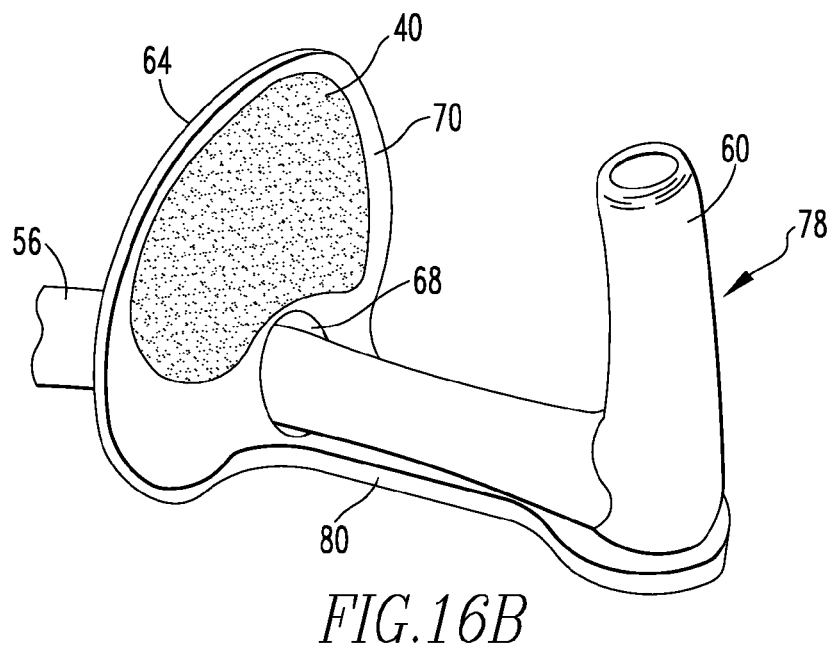
Figure 17:
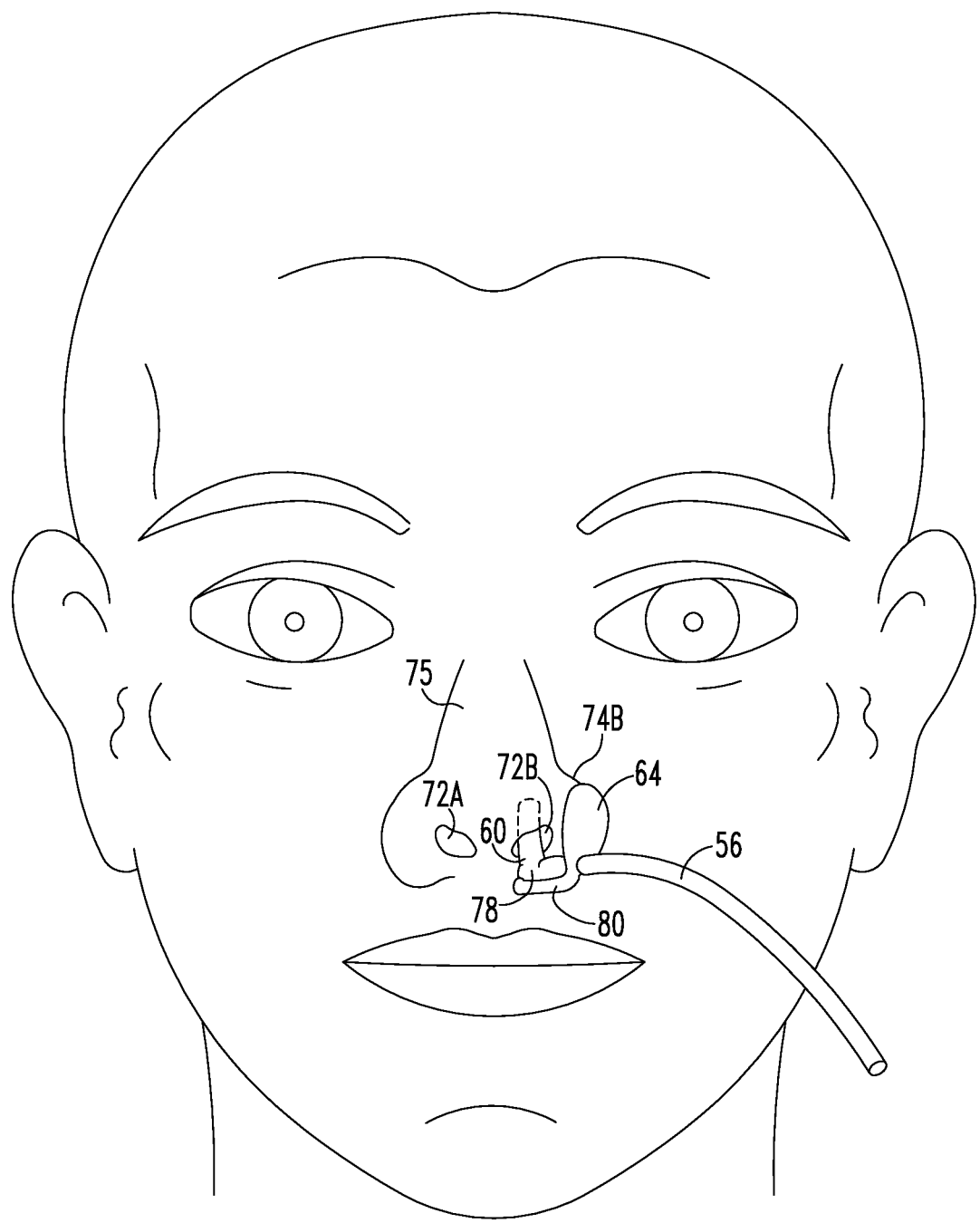
FIG. 17 is a schematic diagram showing the nasal cannula of FIGS. 16A and 16B in use.

The nasal cannulas 54, 76 and 76' shown in FIG. 12-15 are considered double cannulas because each of them includes two nasals inserts 60A and 60B. FIGS. 16A and 16B are isometric views of a nasal cannula 78 according to a further alternate embodiment of the present invention. The nasal cannula 78 is a single cannula and as such is structured to be received within a single nare of the user. FIGS. 16A and 16B show a nasal cannula 78 adapted for insertion into the user's left nare as the shape of the attachment panel 64 generally matches contour of the left alar sidewall 74B of the nose 75 of the user as seen in FIG. 17. As will be appreciated, a nasal cannula 78 adapted for insertion into the user's right nare is also possible. The nasal cannula 78 includes a single fluid delivery tube 56 in fluid communication with a nasal insert 60. The nasal cannula 78 further includes an attachment mechanism 80 having an attachment panel 64 which includes an aperture 68 which receives therethrough the fluid delivery tube 56. As seen in FIGS. 16A and 16B, the end of the attachment mechanism 80 that is opposite the attachment panel 64 is affixed to the bottom of the nasal insert 60. The attachment panel 64 includes an inner surface 70 which has provided thereon an adhesive layer 40 in any of the forms described elsewhere herein. FIG. 17 is a schematic diagram showing the nasal cannula 78 in use wherein the adhesive layer 40 provided on the inner surface 70 of the attachment panel 64 is removeably adhered to the left alar sidewall 74B of the nose 75 of the user.

Figure 18:
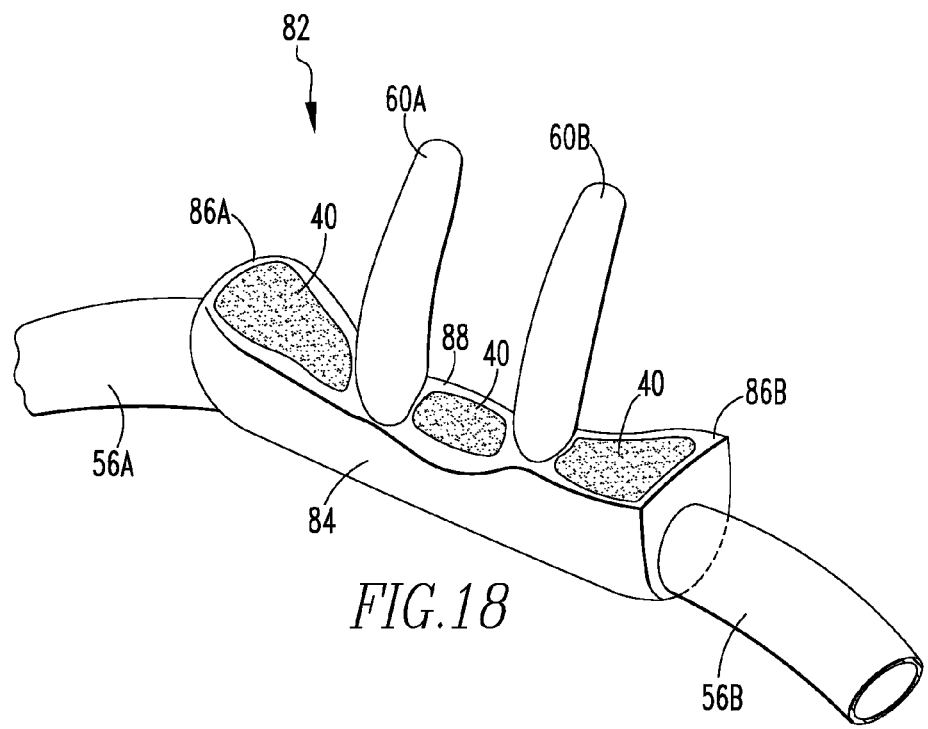
FIG. 18 is an isometric view of a patient interface device in the form of a nasal cannula according to still a further embodiment of the invention.

FIG. 18 is an isometric view of a patient interface device in the form of a nasal cannula 82 according to still a further embodiment of the invention. The nasal cannula 82 includes fluid delivery tubes 56A and 56B connected to opposite ends of a fluid delivery barrel 84. The fluid delivery tubes 56A and 56B are in fluid communication with a source of fluid (not shown), such as an oxygen source, and deliver the fluid, e.g., oxygen, from the source to the fluid delivery barrel 84. First and second nasal inserts 60A and 60B are in fluid communication with the fluid delivery barrel 84 and are structured to be received in the nares of a user. The fluid delivery barrel 84 includes a first outer top surface 86A adjacent to the outside of the nasal insert 60A, a second outer top surface 86B adjacent to the outside of the nasal insert 60B, and an inner top surface 88 between the nasal inserts 60A and 60B. The first outer top surface 86A, the second outer top surface 86B, and the inner top surface 88 each have provided thereon an adhesive layer 40 in any of the forms described elsewhere herein. When in use, the first and second nasal inserts 60A and 60B are inserted within the nares 72A and 72B of the user. In that position, the first outer top surface 86A, the second outer top surface 86B, and the inner top surface 88 are each able to be removeably adhered to the underside of the nose 75 of the user. Specifically, the adhesive layers 40 provided on the first outer top surface 86A and the second outer top surface 86B are able to be removeably adhered to the exterior of the user's nares, and the adhesive layer 40 provided on the inner top surface 88 is able to be removeably adhered to the user's septum. As a result, the nasal cannula 82 is securely held in place while in use.

Figure 19:
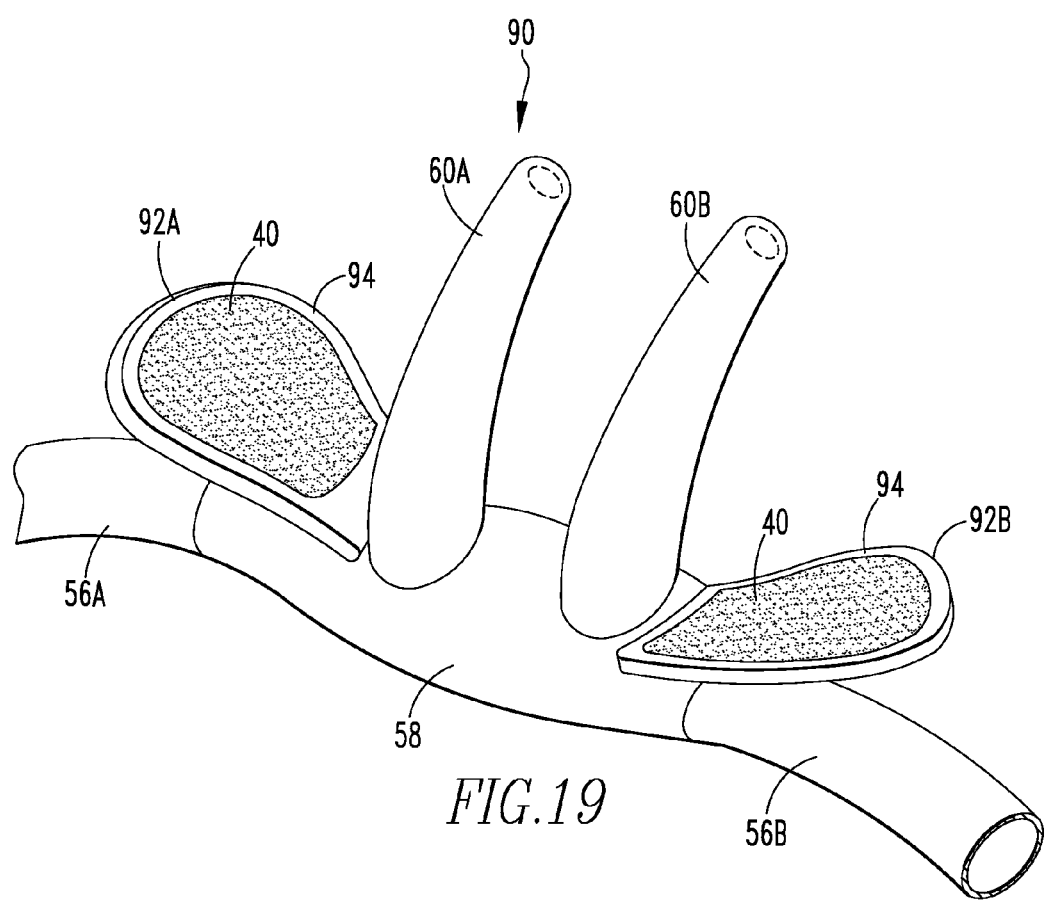
FIG. 19 is an isometric view of a patient interface device in the form of a nasal cannula according to yet a further embodiment of the invention.

FIG. 19 is an isometric view of a patient interface device in the form of a nasal cannula 90 according to yet a further embodiment of the invention. The nasal cannula 90 includes fluid delivery tubes 56A and 56B connected to opposite ends of a fluid delivery barrel 58. The fluid delivery tubes 56A and 56B are in fluid communication with a source of fluid (not shown), such as an oxygen source, and deliver the fluid, e.g., oxygen, from the source to the fluid delivery barrel 58. First and second nasal inserts 60A and 60B are in fluid communication with the fluid delivery barrel 58. The first and second nasal inserts 60A and 60B are structured to be received in the nares of a user so that the fluid, e.g., oxygen, can be delivered from the fluid delivery barrel 58 to the nasal passageway of the user. The nasal cannula 90 further includes a first attachment panel 92A and a second attachment panel 92B that are each connected to the fluid delivery barrel 58. Each attachment panel 92A, 92B includes an inner surface 94 which has provided thereon an adhesive layer 40 in any of the forms described elsewhere herein. When in use, the first and second nasal inserts 60A and 60B are inserted within the nares 72A and 72B of the user. In that position, the attachment panels 92A and 92B are able to be removeably adhered to the exterior of the user's nares by the adhesive layers 40 provided thereon. As a result, the nasal cannula 90 is securely held in place while in use.

Figure 20:
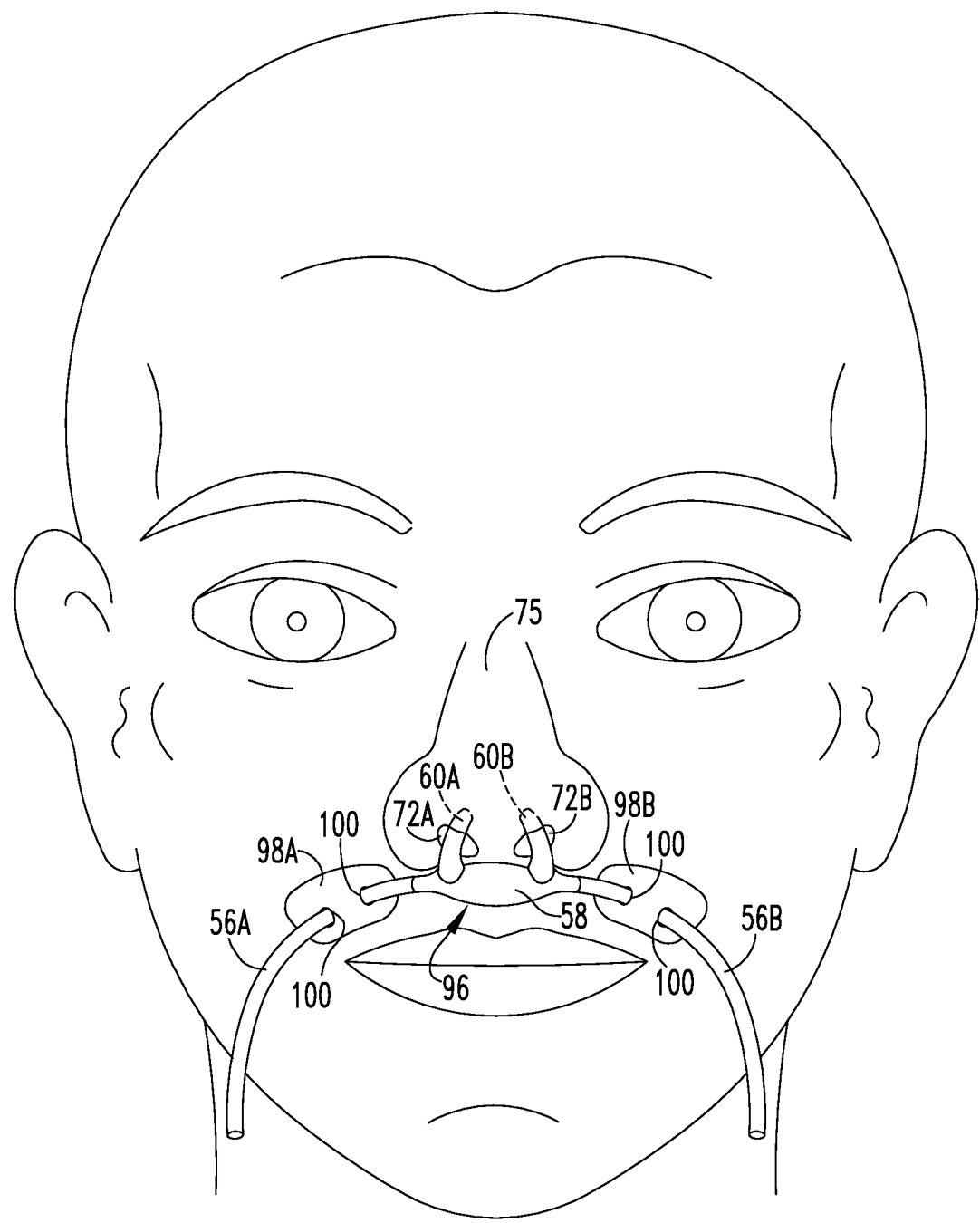
FIG. 20 is a schematic diagram showing of a patient interface device in the form of a nasal cannula according to yet a further embodiment of the invention.

FIG. 20 is a schematic diagram showing of a patient interface device in the form of a nasal cannula 96 according to yet a further embodiment of the invention. The nasal cannula 96 includes fluid delivery tubes 56A and 56B connected to opposite ends of a fluid delivery barrel 58. The fluid delivery tubes 56A and 56B are in fluid communication with a source of fluid (not shown), such as an oxygen source, and deliver the fluid, e.g., oxygen, from the source to the fluid delivery barrel 58. First and second nasal inserts 60A and 60B are in fluid communication with the fluid delivery barrel 58. The first and second nasal inserts 60A and 60B are structured to be received in the nares 72A and 72B of a user so that the fluid, e.g., oxygen, can be delivered from the fluid delivery barrel 58 to the nasal passageway of the user. The nasal cannula 96 further includes a first attachment panel 98A moveably threaded onto the fluid delivery tube 56A and a second attachment panel 98B moveably threaded onto the fluid delivery tube 56. In particular, the fluid delivery tube 56A, 56B is passed through apertures 100 provided in the respective attachment panel 98A, 98B so that the attachment panel 98A, 98B is able to slide along the fluid delivery tube 56A, 56B. As will become apparent below, this allows each attachment panel 98A, 98B to be selectively (and independently) positioned by the user. Each attachment pad 98A, 98B includes an inner surface which has provided thereon an adhesive layer 40 in any of the forms described elsewhere herein. When in use, the first and second nasal inserts 60A and 60B are inserted within the nares 72A and 72B of the user. In that position, the attachment panels 98A and 98B are able to be removeably adhered to the exterior of the user's face (e.g., between the nose and mouth) at positions selected by the user by the adhesive layers 40 provided thereon. As a result, the nasal cannula 96 is securely held in place while in use.

As will be appreciated, each of the components of the nasal cannulas 76, 76', 78, 82, 90 and 96 may be molded out of a suitable polymeric material such as, without limitation, silicone rubber or urethane.

While preferred embodiments of the invention have been described and illustrated above, it should be understood that these are exemplary of the invention and are not to be considered as limiting. Additions, deletions, substitutions, and other modifications can be made without departing from the spirit or scope of the present invention. Accordingly, the invention is not to be considered as limited by the foregoing description but is only limited by the scope of the appended claims.

What is claimed:

1. A patient interface device, comprising:
    at least one seal element; and
    an adhesive layer provided on an outer surface of the at least one seal element and being structured to temporarily bond to the skin of a user of the patient interface device, the adhesive layer comprising a bonding agent having a residual extraction force of between about 50 grams and about 200 grams and the adhesive layer including a coating layer formed by co-curing the bonding agent with at least one layer of a primer material that resists material separation.

2. The patient interface device according to claim 1, wherein the bonding agent is a cross linked polymer gel.

3. The patient interface device according to claim 2, wherein the bonding agent does not include a plasticizer.

4. The patient interface device according to claim 2, wherein the bonding agent is selected from the group consisting of a silicone gel and a polyurethane gel.

5. The patient interface device according to claim 1, wherein the bonding agent has a residual extraction force of about 160 grams.

6. The patient interface device according to claim 1, wherein the bonding agent has a residual extraction force of between about 50 grams and about 160 grams.

7. The patient interface device according to claim 1, wherein the adhesive layer comprises at least one generally annular strip.

8. The patient interface device according to claim 7, wherein the adhesive layer comprises a plurality of concentric generally annular strips.

9. The patient interface device according to claim 1, wherein the adhesive layer has a generally uniform height.

10. The patient interface device according to claim 1, wherein the adhesive layer has a varying height.

11. The patient interface device according to claim 1, wherein the adhesive layer comprises a plurality of deposits of the bonding agent provided on the outer surface of the at least one seal element.

12. A patient interface device, comprising:
a mask having a body;
at least one seal element coupled to the body;
a facial support coupled to the body, the facial support having an engagement surface; and
an adhesive layer provided on the engagement surface, the adhesive layer comprising a bonding agent having a residual extraction force of between about 50 grams and about 200 grams and the adhesive layer including a coating layer formed by co-curing the bonding agent with at least one layer of a primer material that resists material separation.

13. The patient interface device according to claim 1, wherein the bonding agent is a silicone gel and the primer material is a non-gel based silicone.

14. The patient interface device according to claim 13, wherein the primer material is an RTV-2 material or a liquid silicone rubber.

15. The patient interface device according to claim 1, wherein the bonding agent is a polyurethane gel and the primer material is a solvent.

16. The patient interface device according to claim 12, wherein the primer material is acetone.

17. The patient interface device according to claim 12, wherein the bonding agent is a silicone gel and the primer material is a non-gel based silicone.

18. The patient interface device according to claim 17, wherein the primer material is an RTV-2 material or a liquid silicone rubber.

19. The patient interface device according to claim 12, wherein the bonding agent is a polyurethane gel and the primer material is a solvent.

20. The patient interface device according to claim 19, wherein the primer material is acetone.

* * * * *